US006465414B1

(12) United States Patent
Guerin et al.

(10) Patent No.: US 6,465,414 B1
(45) Date of Patent: Oct. 15, 2002

(54) WATER DISPERSIBLE GRANULATES COMPRISING AN ACTIVE HYDROPHOBIC SUBSTANCE

(75) Inventors: Giles Guerin, Eaubonne; Mikel Morvan, Asnieres; Pascal Taquet, Villiers-Sous-Saint-Leu, all of (FR)

(73) Assignee: Rhodia Chimie, Boulogne Billancourt Cedax (FR)

( * ) Notice: Subject to any disclaimer, the term of this patent is extended or adjusted under 35 U.S.C. 154(b) by 0 days.

(21) Appl. No.: 09/600,697

(22) PCT Filed: Jan. 22, 1999

(86) PCT No.: PCT/FR99/00131

§ 371 (c)(1),
(2), (4) Date: Oct. 30, 2000

(87) PCT Pub. No.: WO99/38611

PCT Pub. Date: Aug. 5, 1999

(30) Foreign Application Priority Data

Feb. 2, 1998 (FR) ............................................. 98 01158

(51) Int. Cl.⁷ ............................................... C11D 3/382
(52) U.S. Cl. ....................................... 510/441; 510/444
(58) Field of Search ................................ 510/441, 443, 510/444

(56) References Cited

U.S. PATENT DOCUMENTS

| 4,209,417 A | * | 6/1980 | Whyte .................. 252/174.11 |
| 5,059,542 A | * | 10/1991 | Hirai et al. ................. 436/518 |
| 5,525,367 A | * | 6/1996 | King et al. .................. 426/533 |
| 5,733,272 A | * | 3/1998 | Brunner et al. ............. 604/359 |
| 5,756,447 A | * | 5/1998 | Hall ........................... 510/475 |
| 6,258,297 B1 | * | 7/2001 | Guerin et al. ............ 252/363.5 |

FOREIGN PATENT DOCUMENTS

| EP | 0371 878 | 6/1990 | ............ C08B/37/08 |
| EP | 0 511 037 | 10/1992 | ............ C11D/3/37 |
| EP | 0 609 121 | 8/1994 | ............ C11D/3/37 |
| EP | 0 633 310 | 1/1995 | ............ C11D/3/37 |
| WO | WO 97/15385 A1 | * 5/1997 | |
| WO | WO 97/15385 | * 5/1997 | |
| WO | WO 97/15387 | * 5/1997 | |

OTHER PUBLICATIONS

International Search Report.

* cited by examiner

Primary Examiner—John R. Hardee

(57) ABSTRACT

The invention concerns water dispersible granulates comprising at least a hydrophobic organic active substance (MA) solid or with melting point less than 100° C., in the form of particles, finely divided inside and encapsulated by a solid matrix and a water soluble or water dispersible polypeptide (PP) synthetic or of plant origin and at least an ionic or amphoteric dispersing agent (D) at the active substance/matrix interface. The invention also concerns the method for preparing said granulates in two steps, the first step consisting in preparing a dispersion in water comprising at least a hydrophobic active substance, at least an ionic or amphoteric dispersing agent (D) and at least a water soluble or water dispersible polypeptide (PP) synthetic or of plant origin, and the second step consisting in drying the dispersion until a granulate is formed.

22 Claims, No Drawings

WATER DISPERSIBLE GRANULATES COMPRISING AN ACTIVE HYDROPHOBIC SUBSTANCE

The present invention relates to water-dispersible granules comprising a hydrophobic active material, in particular in liquid form, to a process for preparing them and to their use.

In certain sectors, for example such as the food, cosmetics, agrochemical or paints sector, it is necessary to prepare formulations using active materials in the form of hydrophobic liquid. One of the formulation possibilities is to prepare oil-in-water emulsions of such materials.

However, problems associated with the stability on storage of these emulsions are encountered. Specifically, it is common to observe a more or less pronounced separation of phases of the constituents of the emulsion. In addition, problems of deactivation of the active material may be encountered, said active material possibly degrading by hydrolysis during storage.

Finally, the fact should not be neglected that, in order to be readily manipulable and pumpable, such formulations have relatively low contents of active material and a large amount of water.

As regards certain solid hydrophobic active materials, these may pose problems of difficulties in manipulation due to the escape of said active materials into the atmosphere as dust, or difficulties in sensitivity with respect to the surrounding medium.

One object of the present invention is thus to propose a novel alternative to the problems mentioned above in the sense that the formulations proposed are powders containing high concentrations of active material, in particular in the form of hydrophobic liquid.

Thus, one subject of the invention is water-dispersible granules comprising:
- at least one hydrophobic organic active material (AM) which is solid or has a melting point of less than 100° C., in the form of particles, which is finely divided in and encapsulated by a solid matrix made of a water-soluble or water-dispersible polypeptide (PP) which is synthetic or of plant origin
- and at least one ionic or amphoteric dispersant (D) at the active material/matrix interface.

For good implementation of the invention, said water-dispersible granules comprise
- from 5% to 90%, preferably from 40% to 85% and most particularly from 50% to 80%, of their weight of organic hydrophobic active material (AM),
- from 3% to 90%, preferably from 10% to 60% and most particularly from 15% to 50%, of their weight of water-soluble or water-dispersible polypeptide (PP)
- from 0.02% to 20%, preferably from 0.1% to 10%, of their weight of ionic or amphoteric dispersant (D), said percentages being expressed by weight of solids.

Said particles of active material (AM) can have a mean particle size from about 0.1 $\mu$m to 50 $\mu$m, preferably from about 0.1 $\mu$m to 10 $\mu$m and most particularly from 0.2 $\mu$m to 5 $\mu$m.

Any active material, whether solid or liquid (in unmodified form or dissolved in a solvent) is suitable for the invention provided that it is immiscible or only very sparingly miscible with water.

The term "sparingly miscible" refers to active materials whose solubility in water at pH 7 does not exceed 10% by weight.

Said hydrophobic organic active material preferably has a melting point of less than 100° C.; most particularly, this active material is liquid at ordinary temperature.

Hereinbelow, the expression "active material" will be understood as referring either to the pure active material (which may itself be a solvent) or a mixture of active materials, or to the active material (or a mixture of active materials) dissolved in a solvent.

Examples of active materials used in the food sector which may be mentioned are mono-, di- and triglycerides, essential oils, flavorings and colorings.

Examples of active materials used in the cosmetics sector which may be mentioned are silicone oils belonging, for example, to the dimethicone family.

Examples of active materials used in the paints sector which may be mentioned are alkyd resins, epoxy resins and blocked or unblocked isocyanates.

In the paper sector, mention may be made, for example, of bonding resins and water-repellent resins such as alkylketene dimer (AKD) or alkenylsuccinic anhydride (ASA).

In the detergency sector, mention may be made of silicone antifoams as possible active materials.

In the construction sector, mention may be made of water-repellent products, such as linear, cyclic and/or branched polyorganosiloxanes which can comprise hydroxyl, alkoxy, etc. reactive functions in the chain and/or at the end of a chain.

In the sector of plant-protective active materials, mention may be made of fungicides (iprodione, etc.), herbicides (isoproturon) and insecticides (synthetic pyrethroids, etc.).

It is likewise possible to use active materials such as lubricants for working or deforming materials.

When the active material is a solvent (or a mixture of solvents) or a solution in a solvent (or several solvents), said solvent is immiscible or is only sparingly miscible in water within the meaning indicated previously. Examples which may be mentioned are the solvents used for cleaning or stripping, such as aromatic petroleum fractions, terpenic compounds such as D-limonene or L-limonene, and solvents such as Solvesso®, aliphatic esters, such as the methyl esters of a mixture of acetic, succinic and glutaric acids (mixture of by-product acids from the synthesis of Nylon), liquid paraffins such as liquid petroleum jelly, alkanes, chlorinated solvents and synthetic or natural triglycerides.

Among the water-soluble or water-dispersible synthetic polypeptides (PP) which can constitute the matrix, mention may be made of homopolymers or copolymers derived from the polycondensation of amino acids or amino acid precursors, in particular of aspartic acid and glutamic acid or precursors thereof, and hydrolysis. These polymers can be not only homopolymers derived from aspartic acid or glutamic acid but also copolymers derived from aspartic acid and glutamic acid in all proportions, or copolymers derived from aspartic acid and/or glutamic acid and from other amino acids. Among the copolymerizable amino acids which may be mentioned are glycine, alanine, leucine, isoleucine, phenylalanine, methionine, histidine, proline, lysine, serine, threonine, cysteine, etc.

Among the polypeptides (PP) of plant origin which can constitute the matrix, mention may be made of proteins of plant origin; these are preferably hydrolyzed, with a degree of hydrolysis of less than or equal to 40%, for example from 5% to less than 40%.

Among the proteins of plant origin which may be mentioned as a guide are proteins originating from proteaginous seeds, in particular those of pea, bean, iupin, haricot and lentil; proteins originating from cereal seeds, in particular those of wheat, barley, rye, corn, rice, oat and millet; proteins originating from oleaginous seeds, in particular those of soya, groundnut, sunflower, rape and coconut; proteins originating from leaves, in particular from alfalfa and nettles; and proteins originating from underground reserves of plant organs, in particular those of potato and beetroot.

Said polypeptide (PP) is preferably a protein hydrolyzate obtained from soya or wheat.

The redispersible granules of the present invention contain an ionic or amphoteric dispersant (D).

Among the anionic dispersants which may be mentioned are emulsifiers such as water-soluble salts of alkyl sulfates or of alkyl ether sulfates, alkyl isethionates and alkyl taurates or salts thereof, alkyl carboxylates, alkyl sulfosuccinates or alkyl succinamates, alkyl sarcosinates, alkyl derivatives of protein hydrolyzates, acyl aspartates, and alkyl and/or alkyl ether and/or alkylaryl ether ester phosphates. The cation is generally an alkali metal or alkaline earth metal, such as sodium, potassium, lithium or magnesium, or an ammonium group $NR_4^+$ with R, which may be identical or different, representing an alkyl radical which is unsubstituted or substituted with an oxygen or nitrogen atom.

dispersants such as lignosulfonates, polynaphthalene sulfonates, copolymers comprising units derived from at least one monomer chosen from unsaturated $C_3$–$C_5$ acids, diacids or anhydrides and units derived from at least one unsaturated, linear or branched $C_4$–$C_8$ hydrocarbon.

Among the cationic dispersants which may be mentioned are emulsifiers such as alkyldimethylbenzylammonium halides, alkyldimethylethylammonium halides, etc.

Among the amphoteric dispersants which may be mentioned are emulsifiers such as alkylbetaines, alkyldimethylbetaines, alkylamidopropylbetaines, alkylamidopropyldimethylbetaines, alkyltrimethylsulfobetaines, imidazoline derivatives such as alkyl amphoacetates, alkyl amphodiacetates, alkyl amphopropionates, alkyl amphodipropionates, alkylsultaines or alkylamidopropylhydroxysultaines, the condensation products of fatty acids and of protein hydrolyzates, amphoteric derivatives of alkylpolyamines such as Amphionic XL® sold by Rhône-Poulenc, Ampholac 7T/X® and Ampholac 7C/X® sold by Berol Nobel, and proteins or protein hydrolyzates.

Said dispersant (D) is preferably a protein or a protein hydrolyzate; it can consist of the polypeptide (PP) itself.

According to one embodiment variant of the invention, up to 95%, preferably up to 50%, of the weight of the polypeptide (PP) constituting the matrix is replaced with a water-soluble or water-dispersible ose, oside or polyholoside (O) or a polyelectrolyte (PE) belonging to the family of weak polyacids.

Among the oses which may be mentioned are aldoses such as glucose, mannose, galactose and ribose, and ketoses such as fructose.

Osides are compounds which result from the condensation, with elimination of water, of ose molecules with each other or of ose molecules with non-carbohydrate molecules. Among the preferred osides are holosides which are formed by combining exclusively carbohydrate units and more particularly oligoholosides (or oligosaccharides) which comprise only a limited number of these units, i.e. a number generally less than or equal to 10. Examples of oligoholosides which may be mentioned are sucrose, lactose, cellobiose, maltose and trehalose.

Suitable highly depolymerized polyholosides (or polysaccharides) are described, for example, in the book by P. Arnaud entitled "Cours de Chimie Organique", edited by Gaultier-Villars, 1987. These polyholosides more particularly have a weight-average molecular mass of less than 20,000 g/mol.

Non-limiting examples of highly polymerized polyholosides which may be mentioned are dextran, starch, xanthan gum and galactomannans such as guar or carob, these polysaccharides preferably having a melting point of greater than 100° C. and a solubility in water of between 50 g/l and 500 g/l.

The polyelectrolyte (PE) can be chosen from those derived from the polymerization of monomers which have the following general formula

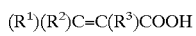

$(R^1)(R^2)C=C(R^3)COOH$ in which formula $R^1$, $R^2$ and $R^3$ are identical or different and represent a hydrogen atom, a hydrocarbon-based radical containing from 1 to 4 carbon atoms, preferably methyl, a —COOH function, a radical —R—COOH, in which R represents a hydrocarbon-based residue containing from 1 to 4 carbon atoms, preferably an alkylene residue containing 1 or 2 carbon atoms, most particularly methylene.

Non-limiting examples which may be mentioned are acrylic acid, methacrylic acid, maleic acid, fumaric acid, itaconic acid and crotonic acid.

Copolymers obtained from monomers corresponding to the above general formula and those obtained using these monomers and other monomers, in particular vinyl derivatives such as vinyl alcohols and copolymerizable amides such as acrylamide or methacrylamide, are also suitable for use. Mention may also be made of the copolymers obtained from alkyl vinyl ether and from maleic acid as well as those obtained from vinylstyrene and maleic acid, which are described in particular in the Kirk-Othmer encyclopedia entitled "Encyclopedia of Chemical Technology"—Volume 18—3rd Edition—Wiley Interscience Publication—1982.

The preferred polyelectrolytes have a low degree of polymerization. The weight-average molecular mass of the polyelectrolytes is more particularly less than 20,000 g/mol. Preferably, it is between 1000 and 5000 g/mol.

The granules according to the present invention have many advantages.

Firstly, their formulation makes it possible to avoid all the problems due to the use of emulsions when the active material (AM) is liquid. Thus, the problems of instability on storage are avoided, in particular such as creaming, flocculation, maturation and coalescence. These various phenomena are described in "Encyclopedia of Emulsions Technology", Volume 1 by Paul Becher, published by Marcel Dekker Inc., 1983.

Another advantage of the present invention is that the concentrations of liquid active materials can be very high. Consequently, during the use of these granules, only a small amount of granules will be sufficient.

Moreover, the formulation according to the invention makes it possible to protect said liquid or solid active material when it is fragile (sensitivity to hydrolysis, volatility, etc.).

The present invention also makes it possible to provide a preformulation in the form of granules, which is thus easier to use than emulsions, for example when said preformulation is added to a formulation in powder form.

In addition, on account of the presence of the dispersant (D), the granules according to the invention have the advantage of dispersing in water to give an emulsion.

Finally, the present invention proposes a solution to the problems of formulation of liquid products which are usually formulated by absorption onto a support. These formulations often have a low concentration of active material and a phase separation may take place between the support and the active material by migration of the active material during storage.

A second subject of the invention consists of a two-step process for preparing water-dispersible granules comprising at least one hydrophobic organic active material (AM) which is solid or has a melting point of less than 1000° C., in the form of particles, which is finely divided in and encapsulated by a solid matrix made of a water-soluble or water-dispersible polypeptide (PP) which is synthetic or of plant origin and at least one ionic or amphoteric dispersant (D) at the active material/matrix interface, the first step consisting in preparing a dispersion in water comprising at least one hydrophobic active material, at least one ionic or amphoteric dispersant (D) and at least one water-soluble or water-dispersible polypeptide (PP) which is synthetic or of plant origin, the second step consisting in drying said dispersion until a granulate forms.

The relative amounts of hydrophobic active material (AM), of ionic or amphoteric dispersant (D) and of water-soluble or water-dispersible polypeptide (PP) which is synthetic or of plant origin, used are such that said dispersion, expressed as dry material, comprises from 5% to 90%, preferably from 40% to 85% and most particularly from 50% to 80%, of their weight of organic hydrophobic active material (AM), from 3% to 90%, preferably from 10% to 60% and most particularly from 15% to 50%, of their weight of water-soluble or water-dispersible polypeptide (PP)

from 0.02% to 20%, preferably from 0.1% to 10%, of their weight of ionic or amphoteric dispersant (D), said percentages being expressed by weight of solids.

The amount of solids in the dispersion is generally between 10% and 70% by weight and preferably between 30% and 60% by weight.

When the active material (AM) is solid, a concentrated dispersion (suspension) can be prepared by introducing the active material (AM) into an aqueous solution containing the dispersant (D) and the water-soluble or water-dispersible polypeptide (PP), with stirring. The concentrated suspension thus prepared, whose mean particle size can range from 1 $\mu$m to 50 $\mu$m, can be ground to obtain a paste with a mean particle size of between 1 $\mu$m and 5 $\mu$m and a viscosity (Brookfield, 20 rpm at 25° C.) of less than 1000 mPa·s.

When the active material (AM) has a melting point of less than 100° C. or when it is in liquid form at ambient temperature, any method for preparing emulsions which is known to those skilled in the art and which is described in "Encyclopedia of Emulsions Technology", Volumes 1 to 3 by Paul Becher, published by Marcel Dekker Inc., 1983, can be used, at the appropriate temperature.

Thus, the method known as direct in-phase emulsification is suitable for preparing the granules according to the invention. It is briefly recalled that this method consists in preparing a mixture containing water, the dispersant (D) and the water-soluble or water-dispersible polypeptide (PP) and then in introducing the active material in liquid form, with stirring.

The emulsion can also be prepared by using colloidal mills such as the Menton Gaulin and Microfluidizer (Microfluidics) mills.

The mean particle size of the emulsion is generally between 0.1 and 10 micrometers and preferably between 0.2 and 5 micrometers.

The emulsification can be carried out at a temperature in the region of ambient temperature, although lower or higher temperatures can be envisaged.

The second step of the preparation process according to the invention consists in drying the dispersion (a suspension or emulsion) thus formulated in order to obtain granules.

The method used to remove the water from the dispersion and to obtain the granules can be carried out by any means known to those skilled in the art.

For example lyophilization, which corresponds to a step of freezing followed by a step of sublimation, or spray-drying, are suitable.

These methods of drying, and more particularly that of spray-drying, are particularly indicated since they make it possible to keep the dispersion in its given form and to obtain granules directly. Water-soluble or water-dispersible proteins of plant origin are particularly suitable for spray-drying, since they are particularly heat-stable.

The spray-drying can be carried out in the usual manner in any known apparatus such as, for example, a spraying tower combining spraying carried out with a nozzle or a turbomixer with a stream of hot gas.

The operating conditions depend on the nature of the matrix, on the heat-sensitivity of the active material and on the sprayer used; these conditions are generally such that the temperature of the product as a whole during the drying operation does not exceed 150° C. and preferably does not exceed 110° C.

The granules obtained can be redispersed in water to again give a dispersion generally having a particle size in the region of that of the initial dispersion.

It should be noted that additives, such as anticaking agents, can be incorporated into the granules at the time of this second drying step. It is recommended to use a filler chosen in particular from calcium carbonate, barium sulfate, kaolin, silica, bentonite, titanium oxide, talc, hydrated alumina and calcium sulfoaluminate.

The examples which follow are given for illustrative purposes.

EXAMPLE 1

Preparation of an Emulsion of Silicone Oil in an Aqueous Solution of Soya Protein A mixture of the following composition is prepared

| | |
|---|---|
| FP940 (soya protein hydrolyzate with a degree of hydrolysis of less than 5%, from Protein Technologies International) | 1.8 parts by weight (as dry material) |
| Silicone oil | 30 parts by weight |
| Deionized water | 68.2 parts by weight | by adding silicone oil to an aqueous 5% by weight solution of FP940.

The solids content is 31.8%.

The mixture is first pre-emulsified using an Ultra-Turrax T25 machine for 1 minute at 9500 rpm.

The actual emulsion is prepared using a microfluidizer ($M^{110}T$ from Microfluidics) under the following conditions: pressure: 600 bar —3 emulsification cycles in the microfluidizer — bath of cold water at the microfluidizer outlet.

The emulsion obtained has a narrow particle size with a median diameter (d50) of 1 μm.

Incorporation of the Matrix

A plant protein hydrolyzed to 15% (FP900 from Protein Technologies International) is incorporated into the prepared emulsion, as polypeptide matrix.

The composition of the emulsion formulated is as follows:

| | |
|---|---|
| FP940 (soya protein hydrolyzate with a degree of hydrolysis of less than 5%, from Protein Technologies International) (emulsifier) | 1.5 parts by weight (as dry material) |
| Silicone oil | 24.75 parts by weight |
| FP900 (soya protein hydrolyzate with a degree of hydrolysis of 15%, from Protein Technologies International) (matrix) | 17.5 parts by weight (as dry material) |
| Deionized water | 56.25 parts by weight |

This formulated emulsion contains 43.75% solids and has a median diameter (d50) of 1 μm.

The composition of this emulsion corresponds to an A/B dry weight ratio of 60/40, in which ratio A and B have the following meaning:

A=(silicone oil+FP940 protein)/total % of solids×100

B=FP900 protein/total % of solids×100

Drying of the Emulsion Formulated

This emulsion is then dried by lyophilization. The granules obtained from this treatment have the following composition:

| | |
|---|---|
| FP940 (soya protein hydrolyzate with a degree of hydrolysis of less than 5%, from Protein Technologies International) (emulsifier) | 3.4 parts by weight |
| Silicone oil | 56.6 parts by weight |
| FP900 (soya protein hydrolyzate with a degree of hydrolysis of 15%, from Protein Technologies International) (matrix) | 40 parts by weight |

Redispersion of the granules in water again gives an emulsion of silicone oil having a fairly homogeneous particle size distribution and a median diameter (d50) of 8 μm.

EXAMPLE 2

The operations described in Example 1 are repeated, using in the step for preparing the emulsion, a liquid petroleum jelly (instead of a silicone oil), in the following proportions:

| | |
|---|---|
| FP940 (soya protein hydrolyzate with a degree of hydrolysis of less than 5%, from Protein Technologies International) | 0.6 part by weight |
| Liquid petroleum jelly | 29.6 parts by weight |
| Deionized water | 69.8 parts by weight |

The emulsion obtained has a solids content of 30.2% and a median particle size diameter (d50) of 1.3 μm.

in the step for incorporating the matrix, a mixture of FP900 protein and sucrose in a 15/85 weight ratio (instead of FP900 protein alone), in the following proportions:

| | |
|---|---|
| FP940 (soya protein hydrolyzate with a degree of hydrolysis of less than 5%, from Protein Technologies International) (emulsifier) | 0.55 part by weight (as dry material) |
| Liquid petroleum jelly | 27.5 parts by weight |
| FP900 (soya protein hydrolyzate with a degree of hydrolysis of 15%, from Protein Technologies International) (matrix) | 1.05 parts by weight (as dry material) |
| Sucrose (matrix) | 6 parts by weight |
| Deionized water | 64.9 parts by weight |

This formulated emulsion contains 35.1% solids and has a median diameter (d50) of 1 μm.

The ratio A/B is 80/20, with

A=liquid petroleum jelly+FP940 protein/total % of solids×100

B=FP900 protein+sucrose/total % of solids×100

The granules obtained after lyophilization have the following composition:

| | |
|---|---|
| FP940 (soya protein hydrolyzate with a degree of hydrolysis of less than 5%, from Protein Technologies International) (emulsifier) | 1.55 parts by weight |
| Liquid petroleum jelly | 78.35 parts by weight |
| FP900 (soya protein hydrolyzate with a degree of hydrolysis of 15%, from Protein Technologies International) (matrix) | 3 parts by weight |
| Sucrose (matrix) | 17.1 parts by weight |

Redispersion of the granules in water again gives an emulsion of liquid petroleum jelly of narrow particle size distribution with a median diameter (d50) of 2.5 μm.

What is claimed is:

1. Water-dispersible granules comprising:
   at least one hydrophobic organic active material (AM) which is solid or has a melting point of less than 100° C., in the form of particles, which is finely divided in and encapsulated by a solid matrix made of a water-soluble or water-dispersible polypeptide (PP) which is a protein of plant origin; and
   at least one ionic, anionic, cationic or amphoteric dispersant (D) at the active material/matrix interface.

2. Granules according to claim 1, comprising:
   from 5% to 90%, of their weight of organic hydrophobic active material (AM),
   from 3% to 90%, of their weight or water-soluble or water-dispersible polypeptide (PP), and
   from 0.02% to 20%, of their weight of ionic or amphoteric dispersant (D),
   said percentage being expressed by weight of solids.

3. Granules according to claim 2, comprising:
   from 50% to 80%, of their weight of organic hydrophobic active material (AM),
   from 15% to 50%, of their weight of water-soluble or water-dispersible polypeptide (PP), and
   from 0.1% to 10%, of their weight of ionic or amphoteric dispersant (D),
said percentages being expressed by weight of solids.

4. Granules according to claim 1, wherein the particles of active material (AM) have a mean particle size from about 0.1 μm to 50 μm.

5. Granules according to claim 4, wherein the particles of active material (AM) have a mean particle size from 0.2 μm to 5 μm.

6. Granules according to claim 1, wherein the hydrophobic organic active material is liquid at ordinary temperature.

7. Granules according to claim 1, wherein the hydrophobic organic active material is an active material from the food sector, from the cosmetics sector, from the paints sector, from the paper sector, from the detergency sector, from the construction sector, or from the plant-protection active materials sector, or a lubricant for working or deforming materials.

8. Granules according to claim 1, wherein said polypeptide (PP) is a protein hydrolyzed with a degree of hydrolysis of less than or equal to 40%.

9. Granules according to claim 8, wherein the protein is a protein hydrolyzate obtained from soya or wheat.

10. Granules according to claim 1, wherein the dispersant (D) is anionic.

11. Granules according to claim 10, wherein the dispersant (D) is a water-soluble salt of alkyl sulfate, water-soluble salt of alkyl ether sulfate, alkyl isethionate, salt of alkyl isethionate, alkyl taurate, salt of alkyl taurate alkyl carboxylate, alkyl sulfosuccinate, alkyl succinamate, alkyl sarcosinate, alkyl derivative of protein hydrolyzate, acyl aspartate, and alkyl phosphate, alkyl ether phosphate, alkylaryl ether ester phosphate, lignosulfonate, polynaphthalene sulfonate, or copolymer comprising units derived from unsaturated $C_3$–$C_5$ acids, diacids or anhydrides and units derived from unsaturated, linear or branched $C_4$–$C_8$ hydrocarbon.

12. Granules according to claim 1, wherein the dispersant (D) is cationic and is an alkyldimethylbenzylammonium halide, or an alkyldimethylethylammonium halide.

13. Granules according to claim 1, wherein the dispersant (D) is amphoteric and is an alkylbetaine, alkyldimethylbetaine, alkylamidopropylbetaine, alkylamidopropyldimethylbetaine, alkyltrimethylsulfobetaine, alkyl amphoacetate, alkyl amphodiacetate, alkyl amphopropionate, alkyl amphodipropionate, alkylsultaine, alkylamidopropylhydroxysultaine, a condensation product of fatty acid and protein hydrolyzate, a protein or a protein hydrolyzate.

14. Granules according to claim 13, wherein the dispersant (D) is a protein or a protein hydrolyzate.

15. Granules according to claim 1, wherein up to 95%, of the weight of the polypeptide (PP) constituting the matrix is replaced with a water-soluble or water-dispersible ose, oside, polyholoside (O), or a polyelectrolyte (PE) which is a weak polyacid.

16. A process for the preparation of water-dispersible granules comprising
  at least one hydrophobic organic active material (AM) which is solid or has a melting point of less than 100° C., in the form of particles, which is finely divided in and encapsulated by a solid matrix made of a water-soluble or water-dispersible polypeptide (PP) which is a protein of plant origin, and
  at least one ionic, cationic, anionic or amphoteric dispersant (D) at the active material/matrix interface,
said process comprising the steps of:
  a) preparing a dispersion in water comprising said hydrophobic active material, said dispersant (D), and said polypeptide (PP), and
  b) drying said dispersion to obtain granules.

17. A process according to claim 16, wherein the relative amounts of hydrophobic active material (AM), of dispersant (D) and of polypeptide (PP) in said dispersion of step a), expressed as dry material, are
  from 5% to 90%, of their weight of active material (AM),
  from 3% to 90%, of their weight of polypeptide (PP)
  from 0.02% to 20% of their weight of dispersant (D),
said percentages being expressed by weight of solids.

18. A process according to claim 16, wherein the amount of solids in the dispersion is between 10% and 70% by weight.

19. A process according to claim 16, wherein the dispersion is a suspension of solid active material (AM) whose mean particle size is between 1 μm and 50 μm, and which has a viscosity (Brookfield, 20 rpm at 25° C.) of less than 1000 mPa·s.

20. A process according to claim 16, wherein the dispersion is an emulsion of liquid active material (AM) whose mean particle size is between 0.11 μm and 10 μm.

21. A process according to claim 16, wherein in step b), the drying of the dispersion is carried out by lyophilization or by spray-drying.

22. A process according to claim 16, wherein anticaking agents are further added in step b) during the drying.

* * * * *